United States Patent [19]

van Winkelhoff et al.

[11] Patent Number: 4,997,830

[45] Date of Patent: Mar. 5, 1991

[54] PHARMACEUTICAL COMPOSITION FOR THE TREATMENT OF PERIODONTITIS

[75] Inventors: Arie J. van Winkelhoff, Houten; Edwin G. Winkel, Amsterdam; Ronald J. Goene, Hoogwoud, all of Netherlands; Lars A. Christersson, Amherst, N.Y.; Joseph J. Zambon, Williamsville, N.Y.; Robert J. Genco, Buffalo, N.Y.

[73] Assignee: The Research Foundation of State University of NY, Albany, N.Y.

[21] Appl. No.: 476,299

[22] Filed: Feb. 7, 1990

[51] Int. Cl.$^5$ ................... A61K 31/415; A61K 31/43
[52] U.S. Cl. .................................. 514/197; 514/398; 514/900; 514/902; 424/54
[58] Field of Search .................... 424/49–58; 514/900–902, 398, 197

[56] References Cited

U.S. PATENT DOCUMENTS

| Re. 33,093 | 10/1989 | Schiraldi et al. | 424/476 |
|---|---|---|---|
| 4,102,998 | 7/1978 | Gutnick | 424/115 |
| 4,568,535 | 2/1986 | Loesche | 424/435 |
| 4,780,320 | 10/1988 | Baker | 424/493 |
| 4,882,167 | 11/1989 | Jang | 424/468 |
| 4,919,939 | 4/1990 | Baker | 424/493 |

OTHER PUBLICATIONS

Walker C.A. 104:65767 R (1986).
Deasy C.A. 112:42395U (1990).
Chodkiewicz C.A. 111:180720B (1989).
Friedman C.A. 108:62501W (1988).
Van Ousten C.A. 106:60754R (1987).
Polson C.A. 105:601H (1986).
Britt C.A. 104:141679F (1986).
Notten C.A. 104:17591G (1986).
Baker C.A. 103:210912V (1985).
Baker C.A. 99:1550629 (1983).
Dahlen C.A. 98:27376N (1983).
Heijl C.A. 96:192982Y (1982).
Kurnman C.A. 95:91056Y (1981).
Slots C.A. 93:107964Yg (1980).
Etude Clinique Comparative entre la Rocéphine (Roche) et la Doxycycline, l'Amoxycilline, l'Erythromycine et l'Association Amoxycilline+Métronidazole en Gynécologie, Georges Gaudin, Gynak. Rdsch., 1985, 25:86–95.
The Therapeutic Use of Metronidazole in Anaerobic Infection: Six Years' Experience in a London Hospital, Susannah Eykyn, Surgery, 1983, pp. 209–214.
Campylobacter Pylori–Therapy Review, A. T. R. Axon, 1989, 24 (Suppl 160), pp. 35–38.
Oral Triple Therapy (OTT) May Effectively Eradicate Campylobacter Pylori (C.p.) in Man, G. Börsch, Abstracts of Papers, Gastroenterology, vol. 94, No. 5, p. A44. (Abstract).
Factors Predicting Abnormal Hysterosalpingographic Findings in Patients Treated for Acute Pelvic Inflammatory Disease, J. Paavonen et al., Int. J. Gynaecol. Obstet., 1985, 23:171–175.
Activité in vitro ee l'Association Amoxicilline–Acide Clavulanique sur les Bactéries Anaérobies, A. Sedallian et al., Pathologie Biologie, Jun. 1988, pp. 678–681.
New Antibiotic Therapies for Human Periodontitis, T. E. Rams et al., J. Periodontal, May 1990, p. 316.
Metronidazole Plus Amoxycillin in the Treatment of *Actinobacillus* Actinomycetemcomitans Associated Periodontitis, Winkelhoff et al., J. Clin. Periodontal, Feb. 1989, 16, pp. 128–131.
New Antibiotics Therapies for Human Periodontitis, T. E. Rams et al., American Acedemy of Periodontology Abstract Presented at Oct. 25, 1989, Annual Meeting.
The Role of Actinobacillus Actinomycetemcomitans in Periodontal Disease, de Graffe, Van Winkelhoff, and Goene, Infection, Jul.–Aug. 1989, 17(4) pp. 269–271.

*Primary Examiner*—Shep K. Rose
*Attorney, Agent, or Firm*—Michael L. Dunn; James F. Mudd; Ellen K. Park

[57] ABSTRACT

A pharmaceutical combination of Metronidazole and Amoxicillin for the treatment of periodontitis. Conventional therapeutic doses of both the Metronidazole and Amoxicillin given as a combination therapy has been unexpectedly found to effectively treat periodontitis.

1 Claim, 1 Drawing Sheet

PHARMACEUTICAL COMPOSITION FOR THE TREATMENT OF PERIODONTITIS

This invention was made in part with U.S. Government support under Grant Number DE04898. The United States Government may have certain rights in this invention.

BACKGROUND OF THE INVENTION

Periodontal diseases in man are bacterial infections in which Gram negative bacteria play an essential role. During the last decade it has become clear that the subgingival microbiota associated with this disease is not uniform, but is different in the various clinical forms. The adult form of periodontitis is often characterized by an anaerobic type of microflora in which, among others, black-pigmented Bacteroides species dominate i.e. *Bacteroides gingivalis* and *Bacteroides intermedius*. On the other hand, in the local form of juvenile periodontitis, *Actinobacillus actinomycetemcomitans* seems to be an etiological agent.

Scientific data have become available that show that A. actinomycetemcomitans is an important etiological factor in several forms of periodontitis. There is substantive evidence that this bacterium is not only involved in localized juvenile periodontitis, but it is also associated with severe adult periodontitis. Studies have revealed that A. actinomycetemcomitans associated periodontitis is more difficult to treat with conventional mechanical therapy than other forms of periodontitis. Conventional mechanical therapy includes supra and subgingival debridement and periodontal surgery. Furthermore, it has been shown that success of treatment in A. actinomycetemcomitans positive patients is strongly associated with the eradication of this microorganism in both juveniles and adults. Since conventional mechanical therapy is not able to arrest the disease progression in most A. actinomycetemcomitans positive patients, antibiotics have been introduced as an adjunct to mechanical and surgical treatment of A. actinomycetemcomitans associated periodontitis. The antibiotic of choice is on of the tetracyclines (tetracycline, doxycycline and minocycline). Disadvantages of the use of tetracyclines relate to the fact that their biological effects are bacteriostatic and include the relatively long period of appliance (2-7 weeks) and often the recolonization of the pockets of A. actinomycetemcomitans after some time.

Therefore, there still exists a need for an effective treatment for A. actinomycetemcomitans related periodontitis.

SUMMARY OF THE INVENTION

The invention comprises, a pharmaceutical composition for use, adjunctive with mechanical procedures, in the treatment of A. actinomycetemcomitans associated periodontal disease, which comprises an effective amount of a combination of Amoxicillin and Metronidazole. The invention also comprises a method for treating A. actinomycetemcomitans associated periodontal disease comprising treating with a pharmaceutical composition comprising the combination of Amoxicillin and Metronidazole.

DETAILED DESCRIPTION OF THE INVENTION

Figure 1A:
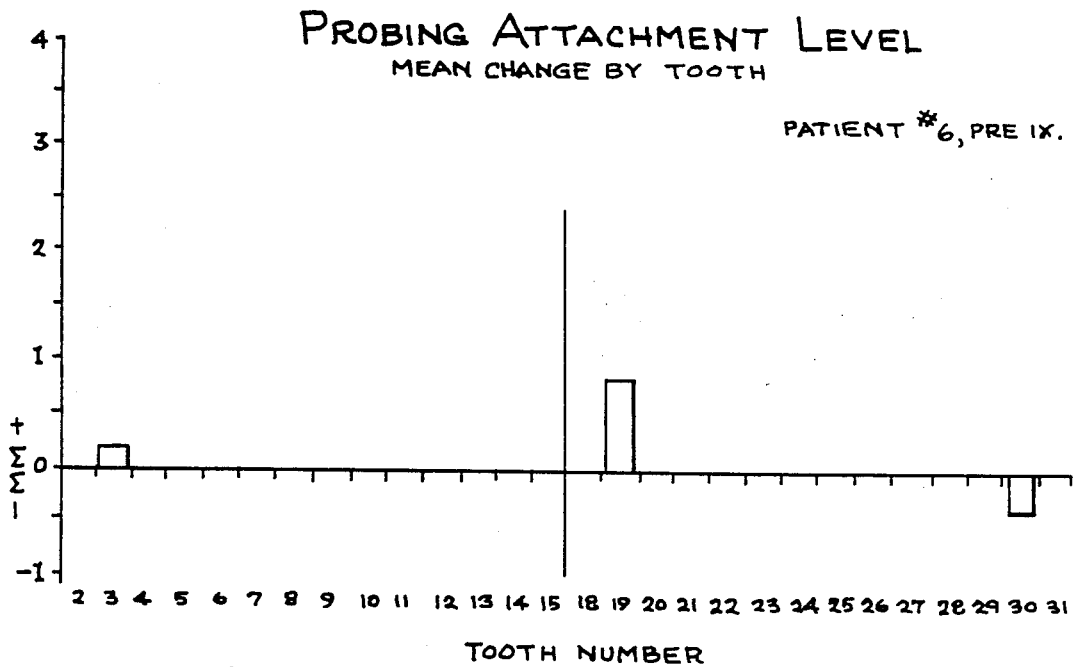
FIG. 1A — depicts the changes in probing attachment obtained by the previous treatment procedures.

An effective amount comprises an amount of the combination of Amoxicillin and Metronidazole such that subgingival elimination of A. actinomycetemcomitans is achieved after about 7 days of administration. Preferably conventional dosages of Amoxicillin and Metronidazole are found effective. By conventional is meant about 250 mg of Metronidazole and between 250 to 375 mg of Amoxicillin three times a day.

The regime for Metronidazole is adapted according to current recommendations from the "1989 Physicians Desk Reference" (PDR) regarding infections mainly caused by anaerobic Gram-negative organisms; adult dosage is up to 30 mg/kg/24 hours (approx. 500 mg, four times a day for a 75-kg adult). Children's dose is adjusted according to weight. The same dose/kg is justified, however, children's dose is listed as up to 50 mg/kg/24 hours for Amebiasis. The treatment is extended to 7 days.

The regime for Amoxicillin is adapted according to current recommendations from PDR regarding infections of the ear, nose and throat due to streptococci, pneumococci and H. influenzae, and organisms closely related to A. actinomycetemcomitans. Adult dosage is up to 500 mg three times a day and up to 40 mg/kg/day for children. Children's dose is adjusted according to weight. The treatment is extended to 7 days.

This treatment of A. actinomycetemcomitans associated periodontitis has superior and unexpected beneficial effects. With a 7 day's therapy of this combination of antibiotics applying conventional dosages, it has been possible to eradicate A. actinomycetemcomitans from the pockets for a period of at least 1 year. Although not wishing to be bound by theory, it is believed that since the clinical improvement and the predictable eradication of A. actinomycetemcomitans was not achieved with either of the single antibiotics it seems that an in vivo synergistic effect is responsible for the effectiveness of the combination therapy.

The following examples and preparations describe the manner and process of using the invention and set forth the best mode contemplated by the inventors of carrying out the invention, but are not to be construed as limiting.

EXAMPLE 1

Patients who previously had received varying amounts of treatment (including systemic antibiotic) and tested positive for A. Actinomycetemcomitans, received 250 mg of Metronidazole plus 375 mg of Amoxicillin, three times a day for a period of 7 days.

Results

A. actinomycetemcomitans was suppressed below detection level in all patients who had received treatment with the combination of Metronidazole plus Amoxicillin (Table 1 below) with the one exception of patient no. 11, who stopped treatment due to serious diarrhea two days after the start of the treatment.

TABLE 1

Clinical description of the patients used in this study and microbiological data before and after subgingival debridement with an adjunctive therapy of Metronidazole and Amoxicillin

| Patient no. | Age (years) | Sex | Clinical diagnosis | Periodontal treatment history | Microbiology Before Treatment | | | Microbiology After Treatment* | | |
|---|---|---|---|---|---|---|---|---|---|---|
| | | | | | Aa | Bg | Bi | Aa | Bg | Bi |
| 1 | 17 | f | LJP | R | + | − | + | − | − | + |
| 2 | 14 | m | LJP | none | + | − | − | − | − | + |
| 3 | 14 | m | LJP | R | + | − | + | − | − | − |
| 4 | 14 | f | LJP | none | + | − | − | − | − | − |
| 5 | 20 | m | LJP | IT + TTC | + | − | − | − | − | −** |
| 6 | 20 | f | LJP | IT + MIN | + | − | − | − | − | − |
| 7 | 23 | f | LJP | none | + | − | − | − | − | + |
| 8 | 25 | m | LJP | none | + | − | + | − | − | − |
| 9 | 25 | f | LJP | none | + | − | − | − | − | − |
| 10 | 33 | f | LJP | IT + S + DOX | + | − | − | − | − | − |
| 11 | 38 | f | LJP | none | + | + | + | + | + | −** |
| 12 | 22 | m | RPP | IT + TTC + S + R | + | − | − | − | − | + |
| 13 | 26 | f | RPP | IT | + | − | + | − | − | − |
| 14 | 28 | f | RPP | IT + MIN | + | − | − | − | − | − |
| 15 | 30 | m | RPP | none | + | − | − | − | − | − |
| 16 | 31 | f | RPp | IT + MIN | + | − | − | − | − | − |
| 17 | 32 | m | RPP | IT + MIN | + | − | − | − | − | − |
| 18 | 35 | f | RPP | IT | + | + | + | − | − | − |
| 19 | 37 | f | RPP | none | + | − | + | − | − | − |
| 20 | 37 | f | RPP | IT | + | + | − | − | − | − |
| 21 | 38 | f | RPP | S + R | + | + | + | − | − | + |
| 22 | 44 | m | RPP | IT | + | − | + | − | − | + | f = female. m = male. LJP = localized juvenile periodontitis. RPP = rapidly progressive periodontitis. IT = initial treatment. S = periodontal surgery. R = recall. TTC = tetracycline hydrochloride. MIN = minocycline. DOX = doxycycline. Aa = *Actinobacillus actinomycetemcomitans*. Bg = *Bacteroides gingivalis*. Bi = *Bacteroides intermedius*. * = subgingival debridement including Amoxicillin plus Metronidazole. ** = severe diarrhea.

The finding that A. actinomycetemcomitans was still undetectable 2–4 months after therapy, suggests a subgingival elimination of this micro-organism. This elimination of A. actinomycetemcomitans was not only observed in the group of LJP patients, but also in the group of RPP patients. Microbiological re-examination of 16 patients 9–11 months after therapy revealed that A. actinomycetemcomitans was still undetectable in the subgingival area. B. gingivalis could not be isolated after therapy, with the exception of patient no. 11. B. intermedium was recovered from 6 patients after therapy ranging from less than 1% up to 5% of the anaerobically cultivated microflora. The clinical condition after treatment improved markedly. In the group of patients with no history of periodontal treatment, the mean probing pocket depths of the sampled sites was reduced from 7.4 mm to 5.5 mm. In the group of patients which had received periodontal treatment in the past, the mean probing pocket depth of the sampled sites decreased from 7.2 mm to 5.3 mm. The number of pockets showing bleeding on pocket probing decreased from 98% pretreatment to 48% after treatment. Moreover, the majority of the residual bleeding pockets after therapy exhibited marked decrease in the degree of bleeding on probing.

EXAMPLE 2

Six patients with LJP, ages 17–22, previously treated for A. actinomycetemcomitans associated severe juvenile periodontal disease were treated with a combination of 500 mg Metronidazole four times a day and 250 mg Amoxicillin three times day. All patients were initially severely infected with subgingival A. actinomycetemcomitans in deep pockets despite previous comprehensive treatment including the administration o systemic tetracycline 250 mg four times a day for up to four weeks.

Results

Localized Juvenile Periodontitis (LJP) is generally recognized as difficult to treat, and several clinical studies indicate an initial failure rate of up to 25%. The association between remaining *Actinobacillus actinomycetemcomitans* after therapy and continuing periodontal deterioration is also well established. They received additional subgingival scaling and root planing to confirm removal of all detectable subgingival deposits.

Figure 1B:
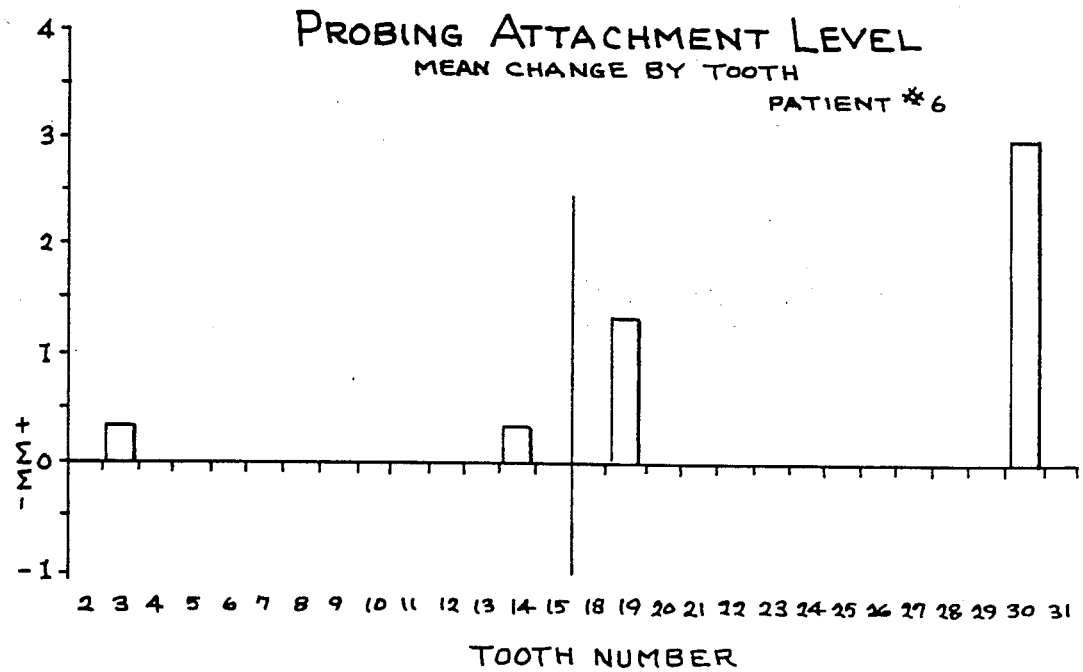
FIG. 1B — illustrates the results obtained three months beyond the treatment with Amoxicillin and Metronidazole.

Immediately following the 7 days of administration of the treatment, all patients were negative for subgingival A. actinomycetemcomitans by microbiologic culture methods. They remained negative for A. actinomycetemcomitans for the 3 month follow up period, when the clinical conditions were critically evaluated by probing pocket depth, probing attachment level measurements and computer assisted radiographic methods. The improvements for the affected teeth can be summarized as follows: a mean pocket reduction of 2.1 mm/subject; a mean increased attachment level of 1.0 mm/subject; and an average reduction of bleeding on probing by 20%. FIG. 1A depicts the changes in probing attachment obtained by the previous treatment procedures (scaling and rootplaning + systemic tetracycline), and FIG. 1B illustrates the results obtained 3 months beyond the treatment with the combination of Amoxicillin and Metronidazole.

This study demonstrates marked reduction of subgingival A. actinomycetemcomitans and resolution of clinical signs of disease in LJP patients through the use of a combination of systemic Metronidazole and Amoxicillin.

EXAMPLE 3

Comparative studies were conducted in 70 A. actinomycetemcomitans positive patients, whom previously were administered a variety of treatment regimes.

Fifteen of these patients were treated previously by conventional mechanical treatment (subgingival scaling & rootplaning), including 4 patients with full mouth surgery (all refractory periodontitis patients); 12 patients were treated conventionally with an adjunct tetracycline therapy (3 weeks) without clinical success; 43 A. actinomycetemcomitans positive patients were previously untreated. All patients were treated conventionally with an adjunct Metronidazole plus Amoxicillin therapy (seven days of 250 mg Metronidazole and 375 mg Amoxicillin, three times a day for 7 days — same regimen for all groups).

Results

The results of the combination therapy are summarized in the attached Tables 2, 3 and 4.

The results of the use of the combination therapy include eradication of A. actinomycetemcomitans in all patients except one for which no explanation is available. A possibility is a bad compliance of the medication. All other patients became free of A. actinomycetemcomitans. Moreover, recolonization of the periodontal pockets by A. actinomycetemcomitans has not been observed for up to 12 months. In addition to the elimination of A. actinomycetemcomitans, B. gingivalis was eliminated from all positive patients. Despite clinical improvement, B. intermedius was found in a substantial number of patients after therapy.

TABLE 2

Group 1, patients previously treated for periodontitis without clinical success and without elimination of A. actinomycetemcomitans. (N = 15).

| Species | Before Treatment | After Treatment | After Metro + Amox |
|---|---|---|---|
| A. actinomycetemcomitans | 15 | 15 | 0 |
| B. gingivalis | 10 | 5 | 0 |
| B. intermedius | 9 | 7 | 3 |

TABLE 3

Group 2. Patients treated for periodontitis with an adjunct therapy of tetracycline (TTC). (N = 17).

| Species | Before Treatment | After Treatment with TTC | After Treatment + Metro + Amox |
|---|---|---|---|
| A. actinomycetemcomitans | 17 | 12 | 0 |
| B. gingivalis | 9 | 2 | 0 |
| B. intermedius | 9 | 4 | 2 |

TABLE 4

Group 3. Patients treated for periodontitis with an adjunct therapy of Metronidazole plus Amoxicillin (N = 43).

| Species | Before Treatment | After Treatment + Metro + Amox |
|---|---|---|
| A. actinomycetemcomitans | 43 | 1 |
| B. gingivalis | 19 | 0 |
| B. intermedius | 23 | 11 |

EXAMPLE 4

Four patients (A–D) are presented. Patients A (33 y.) and B (45 y.) had received periodontal treatment in the past, consisting of scaling and root planing in conjunction with oral hygiene instructions, however without the use of antimicrobiological agents. Despite this treatment these patients showed progressive periodontitis (refractor periodontitis). Patients C (37 y.) and D (36 y.) had no history of periodontal treatment. All four patients were referred to the Clinic for Periodontology Amsterdam for diagnosis and treatment of severe periodontitis in relation to their age. The patients were selected for microbiological investigation on the basis of the following criteria: $\geq$ 4 sites with probing pocket depth of $\geq$ 6 mm, bleeding and/or suppuration on probing of the pocket, and radiographic evidence of 50% loss of alveolar bone in several parts of the oral cavity including angular bony defects. The bleeding tendency after gentle probing was recorded as 0 (no bleeding), 1 (minor bleeding) and 2 (overt, spontaneous bleeding). None of the patients had received antibiotics 6 months prior to the initial subgingival sampling.

Subgingival plaque samples were obtained by paper points from 4 deep pockets in each patient. The samples were pooled and processed by microbiological techniqies for enumeration of A. actinomycetemcomitans and black pigmented Bacteroides species. All four patients were positive for A. actinomycetemcomitans, whereas patients C and D were also infected with B. gingivalis and B. intermedius.

Patients then received initial treatment i.e. oral hygiene instructions and scaling and root planing for 4 to 6 hours in total, with (patients A, B and C) or without (patient D) an adjunct minocycline therapy (100 mg/day for 14 days, with an initial dose of 200 mg). The clinical and microbiological results were evaluated with time intervals of approximately 3 months. The mean probing pocket depth of the four sample sites ranged from 7.5–9 mm. These sites were the same in a patient throughout the evaluation period.

Initially, all sample sites bled on probing, and 50% displayed suppuration.

Clinically none of the patients responded satisfactory to the initial treatment. No significant reduction in probing pocket depth and bleeding on probing was observed in the refractory periodontitis patients A and B. This was in line with the absence of response to initial treatment in the past. Patients C and D did respond to the initial treatment to some extent. However, the clinical situation after initial treatment was not satisfactory including the presence of deep bleeding pockets (Table 5). The initial treatment did not result in the elimination of A. actinomycetemcomitans in either of the patients, despite the use of minocycline (patients A, B and C). Moreover, three of the four patients showed an increase in the percentage and total number of A. actinomycetemcomitans cells after initial treatment (Table 5). Black pigmented Bacteroides species could no longer be isolated from patient C; whereas, patient D was still positive for these microorganisms after the initial therapy. The clinical results of the initial treatment in combination with the microbiological data were the basis for further treatment consisting of surgery (patient C) or continuous mechanical treatment in conjunction with an antibiotic therapy consisting of a combination of two antibiotics, i.e., Metronidazole plus Amoxicillin, 250 mg and 375 mg, respectively, three times a day for 7 days (patients A, B and D). In patient C, surgery resulted in shallow pockets and reduction in the number of bleeding sites. However, A. actinomycetemcomitans was not below detection level, although the number of colony forming units was reduced to only 37 (Table 5). Three months later, this patient showed again an increase in probing pockets depths, an increase in the number of bleeding sites in conjunction with a higher bleeding tendency, despite thorough maintenance care. This clinical decline was associated with a significant increase in the number of A. actinomycetemcomitans cells. At that moment, patient C also received the antibiotic therapy of Metronidazole and Amoxicillin.

In all four patients a significant clinical improvement was obtained after the antibiotic therapy with Metronidazole plus Amoxicillin. With this adjunctive therapy, further reduction in probing pocket depths and reduction in the number of bleeding sites was observed. This clinical improvement was associated with the elimination of subgingival A. actinomycetemcomitans; all four patients had no detectable levels of this microorganism after this therapy and were still negative for this microorganism on repeated sampling after several months (Table 5).

actinomycetemcomitans in LJP patients and that further periodontal destruction is associated with continued presence of A. actinomycetemcomitans.

In patient C a significant reduction in the number of A. actinomycetemcomitans was obtained with the surgical treatment. However, the improved clinical situation of patient C appeared to be not stable after the surgery. This was strongly associated with the outgrowth of A. actinomycetemcomitans. From these data one may conclude that even 37 CFU (Colony Forming Units) recovered of this microorganism in the subgingival area is too many and may lead to further periodontal inflammation and periodontal breakdown. The combination of Metronidazole plus Amoxicillin appeared to be very active against subgingivally occurring A. actinomycetemcomitans, since eradication below detection level of this bacterium was achieved in all four patients. Repeated microbiological examinations in the patients of the present study has revealed no reinfection of the subgingival area.

EXAMPLE 5

As control to the claims of synergistic action for Amoxicillin and Metronidazole data were obtained for 10 A. actinomycetemcomitans positive adult periodon-

TABLE 5

| Period (months) | Pd (mm) | BI | SUP | Aa (cfu) | Bg (%) | Bi (%) | Treatment Choice |
|---|---|---|---|---|---|---|---|
| Patient A, age 33 years, test sites 13M, 22M, 36M, 42D | | | | | | | |
| 0 | 8.5 | 4(2) | 2 | 744,000* | 0 | 0 | IT + Mino |
| 3 | 8.5 | 4(2) | 4 | 286,000 | 0 | 0 | IT + Metro/Amox |
| 6 | 7.0 | 4(1) | 0 | 0 | 0 | 0 | recall |
| 12 | 5.5 | 0 | 0 | 0 | 0 | 0 | recall |
| Patient B, age 45 years, test sites 24M, 37M, 47D, 42D | | | | | | | |
| 0 | 8.5 | 4(2) | 0 | 57,000 | 0 | 0 | IT + Mino |
| 3 | 8.5 | 4(2) | 0 | 171,000 | 0 | 0 | IT + Metro/Amox |
| 6 | 6.0 | 0 | 0 | 0 | 0 | 0 | recall |
| 11 | 6.0 | 1(1) | 0 | 0 | 0 | 0 | recall |
| Patient C, age 37 years, test sites 16M, 17M, 43D, 45M | | | | | | | |
| 0 | 9 | 4(2) | 4 | 60,000 | 1 | 1 | IT + Mino |
| 3 | 5.5 | 4(2) | 0 | 121,000 | 0 | 0 | Surgery |
| 6 | 2.5 | 1(1) | 0 | 37 | 0 | 0 | recall |
| 9 | 4 | 3(2) | 0 | 24,000 | 0 | 0 | Metro/Amox |
| 11 | 3.5 | 1(1) | 0 | 0 | 0 | 0 | recall |
| Patient D, age 36 years, test sites 26M, 21M, 42D, 46D | | | | | | | |
| 0 | 7.5 | 4(2) | 2 | 12,000 | 69 | 6 | IT |
| 3 | 6.0 | 3(2) | 2 | 48,000 | 15 | 4 | IT + Mino |
| 6 | 6.0 | 3(1) | 1 | 31,000 | 1 | 0 | Metro/Amox |
| 8 | 5.0 | 0 | 0 | 0 | 0 | 0 | recall |

Pd, mean probing pocket depth of test sites; BI, number of test sites with bleeding on probing; SUP, number of test sites with suppuration on probing; Aa, *A. actinomycetemcomitans*; Bg, *B. gingivalis*; Bi, *B. intermedius*; IT, initial treatment; Mino, minocycline; metro, Metronidazole; amox, Amoxicillin.
*number of *A. actinomycetemcomitans* cells/0.1 ml sample.

RESULTS

These data show that microbiological monitoring in severe periodontal disease can be a meaningful and practical supplement in the diagnosis, the treatment planning and treatment evaluation of these forms of periodontitis. This study also shows that subgingival elimination of A. actinomycetemcomitans may serve as a microbiological endpoint of periodontal treatment, since improvement of the periodontal condition is clearly associated with the subgingival elimination of A. actinomycetemcomitans. Minocycline was found to be inactive in eliminating A. actinomycetemcomitans from the subgingival area. The above results are also in agreement with previous studies in which it was shown that tetracyclines were not successful in suppressing A.

titis patients. They were treated by conventional techniques with adjunctive systemic antibiotics (4 with Amoxicillin 375 mg three times per day and 6 with Metronidazole 250 mg three times per day).

Results

The results (Tables 6 and 7) clearly indicate that neither of the two antibiotics can predictably eradicate subgingival A. actinomycetemcomitans and further strengthen the claim of synergistic effect.

TABLE 6

Patients treated for periodontitis with an adjunct therapy of Amoxicillin (N = 4).

| Species | Before Treatment | After Treatment + Amoxicillin |
| --- | --- | --- |
| A. actinomycetemcomitans | 4 | 4 |
| B. gingivalis | 2 | 2 |
| B. intermedius | 2 | 1 |

TABLE 7

Patients treated for periodontitis with an adjunct therapy of Metronidazole (N = 6).

| Species | Before Treatment | After Treatment + Metronidazole |
| --- | --- | --- |
| A. actinomycetemcomitans | 6 | 5 |
| B. gingivalis | 4 | 3 |
| B. intermedius | 3 | 3 |

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

What is claimed is:

1. A method for treating periodontal disease characterized by the presence of at least one of *Bacteroides gingivalis*, *Bacteroides intermedius* or *Actinobacillus actinomycetemoomitans*, comprising the step of administering a pharmaceutical composition comprising an effective amount of a combination of Amoxicillin and Metronidazole.

* * * * *

UNITED STATES PATENT AND TRADEMARK OFFICE
CERTIFICATE OF CORRECTION

PATENT NO. : 4,997,830
DATED : March 5, 1991
INVENTOR(S) : Arie J. van Winkelhoff It is certified that error appears in the above-identified patent and that said Letters Patent is hereby corrected as shown below:

Column 10, Claim 1, lines 21-22, "actinomycetemoomitans" should read --actinomycetemcomitans--.

Signed and Sealed this

Twenty-eighth Day of July, 1992

Attest:

DOUGLAS B. COMER

Attesting Officer

Acting Commissioner of Patents and Trademarks